United States Patent [19]
Bednar et al.

[11] Patent Number: 5,945,432
[45] Date of Patent: Aug. 31, 1999

[54] THROMBOLYTIC AGENTS AND THIENOPYRIDINE DERIVATIVES IN ACUTE STROKE

[75] Inventors: Martin M. Bednar, South Burlington, Vt.; Bruce A. Keyt, Pacifica, Calif.; Cordell E. Gross, South Burlington, Vt.

[73] Assignees: The University of Vermont and State Agricultural College, Burlington, Vt.; Grenentech, Inc., South San Francisco, Calif.

[21] Appl. No.: 08/640,667

[22] Filed: May 1, 1996

Related U.S. Application Data

[63] Continuation-in-part of application No. 08/577,047, Dec. 22, 1995, abandoned.

[51] Int. Cl.⁶ .......................... A61K 31/44; A61K 31/38; A61K 31/13; A61K 31/16
[52] U.S. Cl. .......................... 514/301; 514/444; 514/443; 514/663; 514/673; 514/579
[58] Field of Search ..................................... 514/301, 444, 514/443, 663, 623, 579, 1

[56] References Cited

FOREIGN PATENT DOCUMENTS

| 0 352 119 | 1/1990 | European Pat. Off. . |
| WO 89/11531 | 11/1989 | WIPO . |
| WO 93/24635 | 12/1993 | WIPO . |

OTHER PUBLICATIONS

G. Roger Thomas, PhD, Harold Thibodeaux, BS, Carol J. Errett, Julie M. Badillo, BS, Bruce A. Keyt, PhD, Canio J. Refino, BS, Justin A. Zivin, MD, PhD, and William F. Bennett, PhD; "A Long–Half–life and Fibrin–Specific Form of Tissue Plasminogen Activator in Rabbit Models of Embolic Stroke and Peripheral Bleeding"; Stroke, vol. 25, No. 10, Oct. 1994, pp. 2072–2079.

Charles E. Hennekens, MD, Christopher J. O'Donnell, MD, Paul M. Ridker, MD, and Victor J. Marder, MD; "Current Issues Concerning Thrombolytic Therapy for Acute Myocardial Infarction"; JACC, vol. 25, No. 7 (Supplement), Jun. 1995, pp. 18S–22S.

David R. Holmes, Jr., MD, Robert M. Califf, MD, and Eric J. Topol, MD; "Lessons We Have Learned From the GUSTO Trial"; JACC, vol. 25, No. 7 (Supplemental), Jun. 1995, pp. 10S–17S.

Martin M. Bednar, Richard H. Dooley, Maziar Zamani, Diantha B. Howard, and Cordell E. Gross; "Neutrophil and Platelet Activity and Quantification Following Delayed tPA Therapy in a Rabbit Model of Thromboembolic Stroke"; Journal of Thrombosis and Thrombolysis 1995, pp. 179–185.

G. Roger Thomas, PhD, Harold Thibodeaux, BS, Carol J. Errett, Martin M. Bednar, MD, PhD, Cordell E. Gross, MD, and William F. Bennett, PhD; "Intravenous Aspirin Causes a Paradoxical Attenuation of Cerebrovascular Thrombolysis", Stroke, vol. 26, No. 6, Jun. 1995, pp. 1039–1046.

Robert G. Hart, MD, Dianne H. Solomon, MD, J. James Rohack, MD, and William M. Feinberg, MD; "What's new in stroke?"; Texas Medicine, vol. 91, No. 5, May 1995, pp. 46–55.

Peggy Jo Donahue; "Head Off A Stroke; A New Guide To Clot–Dissolving Drugs", Prevention Magazine, 1988, pp. 39–45.

William Feinberg, MD; "Antithrombotic Therapy in Stroke and Transient Ischemic Attacks"; AFP, vol. 40, No. 5, (Supplement), Nov. 1989, pp. 53S–59S.

Jawed Fareed, Demetra D. Callas, Debra Hoppensteadt, Walter Jeske & Jeanine M. Walenga; "Recent developments in antithrombotic agents"; Exp. Opin. Invest. Drugs (1995) 4(5), pp. 389–412.

Sheng–Kun Yao, Judy C. Ober, James J. Ferguson, Jean–Pierre Maffrand, H. Vernon Anderson, L. Maximilian Buja, and James T. Willerson; "Clopidogrel is more effective than aspirin as adjuvant treatment to prevent reocclusion after thrombolysis"; Clopidogrel, Thrombolysis, and Reocclusion, American Physiological Society, 1994, pp. H488–H493.

Richard C. Becker, MD and Jack Ansell, MD; "Antithrombotic Therapy", Arch. Intern. Med., vol. 155, Jan. 23, 1995, pp. 149–161.

Marc Verstraete and Pierre Zoldhelyi; "Novel Antithrombotic Drugs in Development"; Drugs 49(6), 1995, pp. 856–884.

Joan C. Murray, Michael A. Kelly, and Philip B. Gorelick; "Ticlopidine: A New Antiplatelet Agent for the Secondary Prevention of Stroke"; Clinical Neuropharmacology, vol. 17, No. 1, 1994, pp. 23–31.

Charles Warlow, "Ticlopidine, a new antithrombotic drug; but is it better than aspirin for longterm use?"; Journal of Neurology, Neurosurgery & Psychiatry, pp. 185–187.

Karsten Schrör; "Antiplatelet Drugs A Comparative Review"; Drugs 50(1), 1995, pp. 7–28.

Gérard Besson and Julien Bogousslavsky; "Current and Future Options for the Prevention and Treatment of Stroke"; CNS Drugs 3(5), 1995, pp. 351–362.

A. Bernat, F. Dol, J.M. Herbert, M. Sainte–Marie and J.P. Maffrand; "Potentiating Effects of Anticoagulants and Anti–platelet Agents on Streptokinase Thrombolysis in the Rabbit"; Fibrinolysis, Gregory No. 7, 1993, pp. 23–30.

(List continued on next page.)

*Primary Examiner*—Theodore J. Criares
*Attorney, Agent, or Firm*—Wolf, Greenfield & Sacks, P.C.

[57] ABSTRACT

Methods and products are provided for treating thromboembolic stroke. A method involves the administration of a thienopyridine derivative in combination with a thrombolytic agent to a patient suffering from thromboembolic stroke. Preferably the thienopyridine derivative is ticlopidine and the thrombolytic agent is tPA. The method also involves the administration of a thrombolytic agent to a subject who already has circulating plasma levels of a thienopyridine derivative. The product is a pharmaceutical preparation of a thienopyridine derivative and a thrombolytic agent and a pharmaceutically acceptable carrier.

30 Claims, 2 Drawing Sheets

OTHER PUBLICATIONS

Gregory J. Del Zoppo, MD, Brian R. Copeland, MD, Laurence A. Harker, MD, Thomas A. Waltz, MD, Jack Zyroff, MD and Stephen R. Hanson, PhD; "Experimental Acute Thrombotic Stroke in Babboons"; Stroke, vol. 17, No. 6, Nov.–Dec. 1986, pp. 1254–1265.

David G. Sherman, MD, Mark L. Dyken, Jr., MD, Marc Fisher, MD, Michael Gent, PhD, Michael Harrison, MD, and Robert G. Hart, MD; "Antithrombotic Therapy for Cerebrovascular Disorders"; Chest, 102, 4, (Supplement), Oct. 1992, pp. 529S–537S.

Gregory W. Albers; "Antithrombotic Agents in Cerebral Ischemia"; The American Journal of Cardiology, vol. 75, Feb. 23, 1995, pp. 34B–38B.

Martin M. Bednar, MD, Timothy McAuliffe, PhD, Sheila Raymond, AS, and Cordell E. Gross, MD; "Tissue Plasminogen Activator Reduces Brain Injury in a Rabbit Model of Thromboembolic Stroke"; Stroke, vol. 21, No. 12, Dec. 1990, pp. 1705–1709.

Martin M. Bednar, Sheila J. Raymond, and Cordell E. Gross; "Tissue plasminogen activator; Comparison of dose and route of administration in a rabbit model of thromboembolic stroke"; 4 pp.

Cordell E. Gross, MD, Sheila J. Raymond, A.S., Diantha B. Howard, M.S., and Martin J. Bednar, MD; "Delayed Tissue–Plasminogen Activator Therapy in a Rabbit Model of Thromboembolic Stroke"; Neurosurgery, vol. 36, No. 6, Jun. 1995, pp. 1172–1177.

Cordell E. Gross, Diantha B. Howard, Richard H. Dooley, Sheila J. Raymond, Susan Fuller and Martin M. Bednar; "TGF–β1post–treatment in a rabbit model of cerebral ischaemia"; 5 pp.

William F. Bennett, Nicholas F. Paoni, Bruce A. Keyt, David Botstein, Andrew J.S. Jones, Leonard Presta, Florian M. Wurm, and Mark J. Zoller; "High Resolution Analysis of Functional Determinants on Human Tissue–type Plasminogen Activator"; The Journal of Biological Chemistry, vol. 266, No. 8, Mar. 15, 1991, pp. 5191–5201.

Suguru Suzuki, Mamoru Saito, Noboru Suzuki, Hiroyuki Kato, Naoko Nagaoka, Shinji Yoshitake, Yoshi Yui, and Chuichi Kawai, "Intracoronary Infusion of E6010 has More Potent Thrombolytic Activity Than Tissue Plasminogen Activator (t–PA) in Dogs; A Higher Plasma Level of E6010 Than t–PA Causes Potent Thrombolytic Activity"; Journal of Cardiovascular Pharmacology, vol. 22, No. 6, 1993, pp. 834–840.

Peter J. Bugelski, Kei–Lai L. Fong, Anne Klinkner, Janice Sowinski, Glenn Rush and D. Gwyn Morgan; "Uptake of Human Recombinant Tissue–Type Plasminogen Activator by Rat Hepatocytes In Vivo; An Electron Microscope Autoradiographic Study"; Thrombosis Research, vol. 53, No. 3, 1989, pp. 287–303.

J.H. Verheijen, M.P.M. Caspers, G.T.G. Chang, G.A.W. de Munk, P.H. Pouwels, and B.E. Enger–Valk; "Involvement of finger domain and kringle 2 domain of tissue–type plasminogen activator in fibrin binding and stimulation of activity by fibrin"; The EMBO Journal, vol. 5, No. 13, 1986, pp. 3525–3530.

Glenn R. Larsen, Mark Metzger, Kimberlee Henson, Yitzhak Blue, and Patricia Horgan; "Pharmacokinetic and Distribution Analysis of Variant Forms of Tissue–Type Plasminogen Activator With Prolonged Clearance in Rat"; Blood, vol. 73, No. 7, May 15, 1989, pp. 1842–1850.

Douglas E. Vaughan, Paul J. Declerck, Maria De Mol, and Désiré Collen; "Recombinant Plasminogen Activator Inhibitor–1 Reverses the Bleeding Tendency Associated with the Combined Administration of Tissue–type Plasminogen Activator and Aspirin in Rabbits"; J. Clin. Invest., vol. 84, Aug. 1989, pp. 586–591.

Phillip A. Morton, Dwain A. Owensby, Burton E. Sobel, and Alan L. Schwartz; "Catabolism of Tissue–type Plasminogen Activator by the Human Hepatoma Cell Line Hep G2"; The Journal of Biological Chemistry, vol. 264, No. 13, May 5, 1989, pp. 7228–7235.

Burton E. Sobel, MD, Stanley J. Sarnoff, MD, and Denise A. Nachowiak, BA; "Augmented and Sustained Plasma Concentrations After Intramuscular Injections of Molecular Variants and Deglycosylated Forms of Tissue–Type Plasminogen Activators"; Circulation, vol. 81, 1990, pp. 1362–1373.

Burton E. Sobel, MD, Edward M. Geltman, MD, alan J. Tiefenbrunn, MD, Allan S. Jaffe, MD, James J. Spadaro, Jr., MD, Michel M. Ter–Pogossian, PhD, Désiré Collen, MD, and Philip A. Ludbrook, MB, BS; "Improvement of regional myocardial metabolism after coronary thrombolysis induced with tissue–type plasminogen activator or streptokinase"; Circulation, vol. 69, No. 5, May 1984, pp. 983–990.

Michael W. Spellman, Louisette J. Basa, Cordelia K. Leonard, John a. Chakel, and John V. O'Connor; Susanne Wilson and Herman van Halbeek; "Carbohydrate Structures of Human Tissue Plasminogen Activator Expressed in Chinese Hamster Ovary Cells"; The Journal of Biological Chemistry, vol. 264, No. 24, Aug. 25, 1989, pp. 14100–14111.

Benedict, et al., Circulation, vol. 92, 1995, pp. 3032–3034.

N. Eng. J. Med. 1995, Dec. 14, vol. 333(24), pp. 1581–1587.

CA; 120:295826u, 1994.

Anton–Jan van Zonneveld, Harry Veerman, and Hans Pannekoek; "Autonomous functions of structural domains on human tissue–type plasminogen activator"; Proc. Natl. Acad. Sci., vol. 83, Jul. 1986, pp. 4670–4674.

M. Johannessen, V. Diness, K. Pingel, L.C. Petersen, D. Rao, P. Lioubin, P. O'Hara, and E. Mulvihill; "Fibrin Affinity and Clearance of t–PA Deletion and Substitution Analogues"; Thrombosis and Haemostasis F.K. Schattauer Verlagsgesellschaft mbH (Stuttgart), vol. 63(1), 1990, pp. 54–59.

J.H. Verheijen, et al., "Sites in Tissue–Type Plasminogen Activator Involved in the Interaction with Fibrin, Plasminogen and Low Molecular Weight Ligands"; Glenn R. Larsen, et al.; "Pharmacokinetics of Genetically Modified T–PA in Rat"; A. Hotchkiss, et al.; "The Activity of a Single Chain rt–PA Mutant in a Primates and Rabbits"; T. Quertermous, et al.; "Expression of a Recombinant Antibody–Targeted Thrombolytic Molecule"; Fibrinolysis; Molecular Biology, pp. 491.

Désiré Collen, Jean–Marie Stassen, and Glenn Larsen; "Pharmacokinetics andThrombolytic Properties of Deletion Mutants of Human Tissue–Type Plasminogen Activator in Rabbits"; Blood, vol. 71, No. 1, Jan. 1988, pp. 216–219.

David Lau, Gregory Kuzma, Cha–Mer Wei, David Livingston, and Nancy Hsiung, "A Modified Human Tissue Plasminogen Activator with Extended Half–Life In Vivo"; Bio/Technology, p. 734.

Tim J. Ahern, George E. Morris, Karen M. Barone, Patricia G. Horgan, Gregg A. Timony, Lauren B. Angus, Kimberlee S. Henson, John B. Stoudemire, Pennina R. Langer–Safer, and Glenn R. Larsen; "Site–directed Mutagenesis in Human Tissue–Plasminogen Activator"; The Journal of Biological Chemistry, vol. 265, No. 10, Apr. 5, 1990, pp. 5540–5545.

THROMBOLYTIC AGENTS AND THIENOPYRIDINE DERIVATIVES IN ACUTE STROKE

RELATED APPLICATIONS

This is a continuation-in-part of Ser. No. 08/577,047 filed on Dec. 22, 1995, entitled Thrombolytic Agents and Thienopyridine Derivatives in Acute Stroke, now abandoned. The contents of the parent application is hereby expressly incorporated by reference.

BACKGROUND OF THE INVENTION

Stroke is a neurological disorder which involves an acute injury to the cells of the brain as a result of the interruption of blood flow to the brain. When the blood supply to the brain is interrupted, the result is neuronal dysfunction and neuronal death or infarction. This interruption in the blood supply to the brain which is often referred to as ischemia, may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

Cerebral ischemia may result in either transient or permanent deficits. A transient ischemic attack (TIA) is a temporary neurologic deficit which clears in less than 24 hours. TIAs generally last less than 30 minutes. Symptoms of TIA include numbness or weakness of face or limbs, loss of the ability to speak clearly and/or to understand the speech of others, a loss of vision or dimness of vision, and a feeling of dizziness. A stroke is defined as a loss of neurons that usually results in a neurologic deficit that may improve but does not entirely resolve. The seriousness of the neurological damage in a patient who has experienced cerebral ischemia depends on the intensity and duration of the ischemic event. Ischemic events may involve single or multiple brain regions.

The likelihood of a patient having a subsequent stroke after experiencing a TIA or stroke is much greater than that likelihood in an individual who has not had a TIA or stroke. As a result of the higher likelihood of experiencing a stroke, doctors often provide medical treatments to patients who have had TIAs or strokes in order to prevent the development of a subsequent stroke.

Three types of stroke disorders have been identified, based on the underlying mechanisms involved in causing the ischemia, including thrombosis, embolism, and hemorrhage. Because it is often difficult to discern whether a stroke is caused by thrombosis or embolism, the term "thromboembolism" is used to cover both of these types of stroke. The term thromboembolism will be used throughout this patent application to describe thrombotic and embolic strokes. Determining the mechanism causing ischemia in a particular patient is an important step in the determination of an appropriate therapeutic profile for treating the ischemic disorder or for preventing subsequent strokes. Thromboembolic stroke is due to the occlusion of an extracranial or intracranial blood vessel by a thrombus or embolus. An embolus refers to any clot, debris or plaque which embolizes.

Hemorrhagic stroke, unlike thromboembolic stroke, is caused by the rupture of a vessel in the subarachnoid space or intracerebral tissue. This necessitates using different drugs for treating hemorrhagic stroke than for treating thromboembolic stroke. Most treatment methods for thromboembolic stroke involve the administration of drugs which can lyse the clot or prevent formation of subsequent clots. However, most drugs that lyse or prevent formation of blood clots also exacerbate bleeding. As a result, such drugs, which are useful in thromboembolic stroke, are contraindicated in treating hemorrhagic stroke because these compounds would induce further hemorrhaging (bleeding).

Antiplatelet agents, which inhibit platelet aggregation, are often used to prevent thromboembolic stroke in patients who have experienced a TIA or stroke. However, these agents only reduce the risk of subsequent attacks by approximately 25%. The most commonly used antiplatelet agents to prevent stroke include aspirin, ticlopidine and dipyridamole.

Anticoagulation agents also are used for preventing thromboembolic stroke. Anticoagulants, which prevent the coagulation of blood components and thus prevent clot formation, are used much more cautiously than antiplatelet agents. Anticoagulants are so effective at inhibiting blood clot formation that they may encourage or result in hemorrhage in the brain, causing hemorrhagic stroke. The most common anticoagulation agents used to prevent subsequent strokes are coumarin and heparin.

Although both antiplatelet agents and anticoagulation agents are effective in preventing subsequent cerebral ischemic events in patients who have previously experienced TIA or a completed stroke, thrombolytic agents are the therapy of choice during the first few hours after stroke onset. Thrombolytic agents function by lysing the clot which causes the thromboembolic stroke. Commonly used thrombolytic agents include streptokinase and tissue plasminogen activator (tPA).

Native t-PA is composed of 5 functionally distinct domains. These domains include the finger (amino acids 1–44), growth factor (amino acids 45–91), Kringle-1 (amino acids 92–173), Kringle-2 (amino acids 180–261), and serine protease (amino acids 264–527) domains. Deletion of the finger and growth factor domains results in t-PA having a lower binding affinity for fibrin than it would in the absence of deletion, suggesting that these domains may play a role in the binding of t-PA to fibrin. [Zonneveld, A J et al., *PNAS* 83, 4670–4677 (1986); Verheijen, J. H. et al., *Embo J.* 5,3525–30 (1986)]. Although these studies also initially showed the Kringle 2 domain to have a potential role in fibrin binding, more recent studies involving mutations, suggest that the Kringle-2 domain may not be involved in fibrin binding but rather may be responsible for t-PA binding to lysine. [Bennet W. F. et al. *J. Biol. Chem.* 266, 5191–5201 (1991)]. The serine protease domain which is believed to be responsible for the enzymatic activity of t-PA, has been shown to be involved in both the determination of fibrin specificity as well as fibrin binding. [Bennet et al., 1991, Supra)].

T-PA functions as a serine protease which converts plasminogen to plasmin in the presence of fibrin. Fibrin is believed to be a critical component of the protease activity because t-PA does not catalyze this conversion efficiently in the absence of fibrin. Sobel, B. E. et al., has hypothesized that it is this fibrin specificity of t-PA which allows t-PA to induce a local affect without causing systemic induction of plasminogen activation. [*Circulation* 69, 983–990 (1984)]. The phenomenon of local activation is unique to t-PA as opposed to other non-fibrin-specific thrombolytic agents, such as streptokinase and urokinase, which tend to induce a higher systemic plasminogen activation.

Native t-PA generally exists in either a single chain or a double chain form, both of which are functionally active.

The single chain form of t-PA includes all 527 amino acids. The double chain form is produced by cleavage of the single chain form between amino acid positions 275 and 276. Although both the single and double chain forms are functionally active, each of the different forms of t-PA exhibit a different level of enzymatic activity in the absence of fibrin. The double chain form exhibits greater enzymatic activity than does the single chain form. In the presence of fibrin however, both the single and double chain forms of t-PA are equally active. [Lijnen et al., Thromb. Haemost. 64, 61–8 (1990), and Bennett et al., 1991, Supra)].

Acute stroke is an urgent medical condition with a small therapeutic window of time (possibly as brief as 4–6 hours) in which treatment is beneficial. Clot lysing drugs are believed most useful if administered during this window of time in order to at least partially restore cerebral blood flow within the compromised region and to sustain neuronal viability.

Recently, investigators have begun to study the effect of thrombolytic agents as a treatment for acute thromboembolic stroke during this critical window of time. The studies have revealed that tPA is effective in improving neurological outcome in patients who are treated within the first few hours of onset of the stroke. A significant clinical improvement was seen in patients who were administered tPA within 90 minutes of stroke onset. These findings indicate that tPA may be an effective clinical treatment method for acute thromboembolic stroke. Although tPA appears to be both safe and efficacious, there is a need to improve both the rate and speed of restoration of blood supply to the brain.

In an effort to improve treatment for acute stroke, researchers set out to determine whether combining thrombolytic therapy with other therapies would improve the physiological outcome in stroke patients. A study by Thomas et al., Stroke V. 26, page 1039–1046 (1995) looked at the effect of combining aspirin, an antiplatelet agent, with tPA, a thrombolytic agent, in a rabbit model of thromboembolic stroke. Although it has been known in the art that this combination of thrombolytic therapy with antiplatelet therapy in acute myocardial infarction has been beneficial to the patient and reduced the death rate by greater than 50% in myocardial infarction patients, the authors in the Thomas study found that aspirin actually antagonized the effect of tPA in thromboembolic stroke. Because aspirin is often used for preventing stroke in patients who have previously suffered a stroke or a TIA, the finding that aspirin actually antagonizes tPA induced clot lysis and exacerbates brain injury and acute stroke may have devastating results in these patients. The findings suggest that tPA should not be used in combination with antiplatelet agents.

SUMMARY OF THE INVENTION

The invention involves the surprising finding that a class of antiplatelet agents, thienopyridine derivatives, enhance the efficacy of thrombolytic agents in treating acute stroke and reducing brain injury.

In one embodiment, the invention is a method for treating thromboembolic stroke. The method involves administering to a subject experiencing an acute thromboembolic stroke a thienopyridine derivative in combination with a thrombolytic agent in an amount effective to reduce brain injury which would otherwise occur as a result of the stroke. In one embodiment, the thienopyridine derivative is ticlopidine and the thrombolytic agent is tPA. In a preferred embodiment the thienopyridine derivative is administered orally and the thrombolytic agent is administered intravenously. In another embodiment the thienopyridine derivative and thrombolytic agent are administered to the subject within a first 4–6 hours after the subject experienced the thromboembolic stroke. In one embodiment the thienopyridine derivative is administered in an amount between 100 and 1000 mg every twelve hours. In a preferred embodiment the thienopyridine derivative is ticlopidine and is administered in an amount of 250 mg every twelve hours. In one embodiment the thrombolytic agent is administered in an amount between 0.05 mg/kg and 1.5 mg/kg. In a preferred embodiment the thrombolytic agent is tPA and is administered in an amount of 1.1 mg/kg. In one embodiment the thrombolytic agent is recombinant tPA. In another embodiment the thrombolytic agent is a modified tPA. In one embodiment the modified tPA is T103N, N117Q, KHRR (296–299) AAAA t-PA. In another embodiment the modified tPA is a vampire bat t-PA selected from the group consisting of Bat-Pa(H), Bat-Pa(I), and Bat-PA(L). In yet another embodiment the modified tPA is C84S t-PA.

In another embodiment of the invention a pharmaceutical preparation of a thienopyridine derivative and a thrombolytic agent is provided. The pharmaceutical preparation is formulated for oral administration in one embodiment. In another embodiment the pharmaceutical preparation is formulated for intravenous administration. In one embodiment the thrombolytic agent is recombinant tPA. In another embodiment the thrombolytic agent is a modified tPA. In one embodiment the modified tPA is T103N, N117Q, KHRR (296–299) AAAA t-PA. In another embodiment the modified tPA is a vampire bat t-PA selected from the group consisting of Bat-Pa(H), Bat-Pa(I), and Bat-PA(L).

According to another embodiment of the invention a method for treating thromboembolic stroke is provided. The method involves the step of administering to a subject who has circulating plasma levels of a thienopyridine derivative and is experiencing a thromboembolic stroke, a thrombolytic agent in an amount effective to reduce brain injury which would otherwise occur as a result of the stroke. In one embodiment the circulating plasma level of the thienopyridine derivative is between 0.6 and 0.9 mg/liter. In another embodiment the thrombolytic agent is administered intravenously in an amount between 0.05 mg/kg and 1.5 mg/kg. In a preferred embodiment the thrombolytic agent is tPA and is administered intravenously in an amount of 1.1 mg/kg. In one embodiment the thrombolytic agent is recombinant tPA. In another embodiment the thrombolytic agent is a modified tPA. In one embodiment the modified tPA is T103N, N117Q, KHRR (296–299) AAAA t-PA. In another embodiment the modified tPA is a vampire bat t-PA selected from the group consisting of Bat-Pa(H), Bat-Pa(I), and Bat-PA(L).

DETAILED DESCRIPTION OF THE INVENTION

In one embodiment, the invention involves a method for treating thromboembolic stroke by administering to a subject experiencing an acute thromboembolic stroke a thienopyridine derivative in combination with a thrombolytic agent in an amount effective to reduce brain injury which would otherwise occur as a result of the stroke. It has previously been established that the administration of the antiplatelet agent, aspirin, antagonizes the thrombolytic action of tPA in a model of thromboembolic stroke. The present invention involves the unexpected finding that another class of antiplatelet agents, thienopyridine derivatives, do not antagonize the effect of thrombolytic agents in a model of thromboembolic stroke. Additionally, the administration of thienopyridine derivatives in conjunction with thrombolytic agents reduces brain injury which would otherwise occur as a result of the stroke.

According to another embodiment of the invention, a method for treating thromboembolic stroke is provided. The method involves the step of administering to a subject who has circulating plasma levels of a thienopyridine derivative and is experiencing a thromboembolic stroke, a thrombolytic agent in an amount effective to reduce brain injury which would otherwise occur as a result of the stroke.

The methods of the invention are directed to the treatment of acute thromboembolic stroke. An acute stroke is a medical syndrome involving neurological injury resulting from an ischemic event, which is an interruption in the blood supply to the brain. Acute stroke may be thromboembolic or hemorrhagic. The methods of the invention are limited to thromboembolic stroke which results from the occlusion of blood vessels by a thrombus or embolism.

According to another embodiment of the invention a pharmaceutical preparation of a thienopyridine derivative, a thrombolytic agent and a pharmaceutically acceptable carrier is provided.

Thienopyridine derivatives, which are potent inhibitors of platelet aggregation, are actually prodrugs because they are inactive in vitro and active in vivo, indicating that at least one active metabolite is involved in the inhibition of platelet aggregation. Because a portojugular shunt abolishes the anti-aggregating effects of thienopyridine derivatives, it is believed that the metabolic activation occurs in the liver. The inhibition of platelet aggregation by thienopyridine derivatives is irreversible.

Thienopyridine derivatives function by interfering with platelet aggregation which is induced by a variety of agonists, in particular adenosine diphosphate (ADP). Studies have shown that thienopyridines are also capable of inhibiting platelet aggregation induced by the following agonists; collagen, epinephrin, thrombin, platelet activating factor, serotonin, and thromboxane. Although it has been hypothesized that these compounds (or their active metabolites) exert a direct effect on the 2-methylthio-ADP binding ADP receptor subtype at the platelet membrane thus interfering with ADP agonists, the exact biochemical mechanism of action is unknown. Another hypothesis suggests that thienopyridine derivatives prevent the interaction of fibrinogen with its platelet surface receptor glycoprotein.

The thienopyridine derivatives of the invention include known thienopyridines such as ticlopidine and clopidogrel as well as active metabolites of thienopyridine derivatives which interfere with the ADP, collagen, epinephrine, thrombin, or platelet activating factor mediated platelet activation.

Ticlopidine or 5-[(2-chlorophenol) methyl]-4,5,6,7-tetrahydrothieno-3,2-C] pyridine has the following structural formula:

Clopidogrel, $C_{16}$—$H_{16}$—Cl—N—$O_2$—S, has the CAS Registry number 90055-48-4 and the following formula: thieno(3,2-c)pyridine-5(4H)-acetic acid, a-(2-chlorphenyl)-6,7-dihydro-,methyl ester.

Thrombolytic agents have been used in the treatment of acute venous thromboembolism and pulmonary emboli and are well known in the art (e.g. see Hennekens et al, *J Am Coll Cardiol*; v.25 (7 supp), p. 18S–22S (1995); Holmes, et al, *J Am Coll Cardiol*; v.25 (7 suppl), p. 10S–17S(1995)). Thrombolytic agents include direct acting agents such as streptokinase and urokinase, and second generation agents such as tissue plasminogen activator (tPA).

In a preferred embodiment of the invention t-PA is the thrombolytic agent. The mature t-PA polypeptide has 527 amino acids, at least 17 (Asn) of which have been shown to be linked with carbohydrate structures. Spellman et al., have identified several of these carbohydrates, including a high-mannose structure on amino acid 117, and di-tri-and tetra-antennary N-acetyllactosamine-type structures on amino acids 184 and 448 [*J. Biol. Chem.* 264 (24) 14100–14111 (1989)].

"t-PA" as used herein includes native t-PA and recombinant t-PA, as well as modified forms of t-PA that retain the enzymatic or fibrinolytic activities of native t-PA. The enzymatic activity of t-PA can be measured by assessing the ability of the molecule to convert plasminogen to plasmin. The fibrinolytic activity of t-PA may be determined by any in vitro clot lysis activity known in the art, such as the purified clot lysis assay described by Carlson, et. al., *Anal. Biochem.* 168, 428–435 (1988) and its modified form described by Bennett, W. F. Et al., 1991, Supra, the entire contents of which are hereby incorporated by reference.

Recombinant t-PA has been described extensively in the prior art. Several forms of recombinant t-PA are commercially available such as ACTIVASE®.

Modified forms of t-PA ("modified t-PA") have been characterized and are known to those skilled in the art. Modified t-PA includes, but is not limited to, variants having deleted or substituted amino acids or domains, variants conjugated to other molecules, and variants having modified glycosylation. Several preferred modified t-PAs have been described in PCT Publication No. WO93/24635; EP 352, 119; EP382174; and Suzuki et al., *J. Cardiovasc. Pharmacal.* 22, 834–840 (1993). Each of these references is hereby incorporated by reference.

Briefly, PCT Publication No. WO93/24635 discloses t-PA variants having an extra glycosylation site at any of the amino acid positions 103–105 and the native glycosylation site removed at position 117 of the native human t-PA. The amino acid number refers to the amino acid in that position of the mature, wild-type t-PA polypeptide as disclosed in U.S. Pat. No. 4,766,075. These variants have extended circulatory half lives and exhibit substantially the same or improved fibrin binding affinity and fibrinolytic potency as compared to wild-type human t-PA. The disclosed variants may also include at least one amino acid substituted in the 296–299 position with alanine and/or a substitution of the amino acids at positions 274–277 of wild type t-PA (phenylalanine, arginine, isoleucine, lysine) with leucine, histidine, serine, and threonine, respectively. One particularly effective type of variant disclosed in the reference is a triple mutant variant of wild type t-PA. The first mutation in a triple mutant is the addition of one glycosylation site at least one of the amino acid positions 103–105 by e.g., substituting the native amino acid sequence 103 with an asparagine as part of an Asn-X-Ser or Asn-X-Thr tripeptidyl sequence, wherein X is any amino acid except proline. The second mutation involves the removal of a glycosylation site at native amino acid site 117 (Asn) and replacing it with another amino acid, preferably glutamine. The third mutation is the replacement of native amino acids 296–302 with other amino acids. The most effective of the triple mutant variants is the specific molecule, T103N, N117Q, KHRR (296–299) AAAA t-PA (TNK t-PA).

EP 352,119 discloses Vampire Bat t-PA's (Bat-Pa (H), (I), and (L)). Vampire bat-Pa's are variants of native t-PA having a variety of sequence modifications. Although the Bat-Pa variants are structurally distinct from t-PA because they lack the Kringle 2 domain and plasmin-sensitive processing site, these variants are functionally similar to native t-PA. They are however, more potent than native t-PA.

Suzuki et al., *J. Cardiovasc. Pharmacal.* 22, 834–840 (1993) disclose t-PA variants in which a cysteine at position 84 of the growth factor domain of native t-PA is replaced by serine (C84S t-PA). Although this variant retains the functional activity of native t-PA, it has been shown to have a longer in vivo half life than native t-PA.

Native t-PA is cleared from the plasma quite rapidly. At least one receptor in the liver is involved in the clearance of t-PA. [Bugelski, P. J. et al., *Throm. Res.* 53, 287–303 (1989); and Morton P. A. et al., *J. Biol. Chem.* 264, 7228–7235 (1989)]. The responsibility for clearance of the t-PA by the liver has been localized to the finger and growth factor domains as well as to the carbohydrate chains linked to the amino acid backbone. [Collen et al., *Blood* 71, 216–219 (1988); Larsen et al., *Blood* 73, 1842–1850 (1989); and Lau et al., *Biotechnology* 6, 734 (1988)].

The rapid clearance of t-PA from the blood presents a problem to the therapeutic use of the drug because it becomes difficult to maintain adequate therapeutic levels of t-PA in the blood. As a result, patients in need of t-PA treatment must be given a continuous intravenous administration in order to maintain therapeutic levels of t-PA.

Researchers have attempted to develop functional t-PA molecules which have decreased clearance rates. The term "clearance rate" as used herein means the rate at which the t-PA is removed from the bloodstream. The clearance rate is measured with respect to native t-PA, such that decreased clearance rates indicate that the t-PA variant is cleared more slowly than native t-PA, and increased clearance rates indicate that the t-PA variant is cleared more rapidly than native t-PA. As a result, several variants of t-PA have been developed which retain t-PA functionality but have reduced clearance rates.

T-PA variants having deleted or substituted amino acids or domains, have been found to have reduced clearance rates. These variants include t-PA molecules with deleted amino acids or domains, such as those described in Johannessen et al., Throm. *Haemonstas* 63, 54–59 (1990); Collen et al., 1988, Supra; and Sobel et al., *Circulation* 81, 1362–73 (1990); t-PA molecules which have amino acid substitutions in the regions of 63–72 and 42–49, such as those described in Ahern et al., *J. Biol. Chem.* 265, 5540 (1990); and t-PA molecules which have a glutamic acid substituted for the arginine at position 275 of the native t-PA molecule such as that described in Hotchkiss et al., *Throm. Haemost.*, 55, 491 (1987).

T-PA molecules conjugated to other molecules have also been found to have decreased clearance rates. For example, conjugation of t-PA to polyethylene-glycol has been shown to reduce the clearance rate of t-PA, as disclosed in EP-A304,311. Conjugation of a t-PA molecule to a monoclonal antibody has been shown to increase the half-life of t-PA in vivo. [EPA339,505].

Modification of glycosylation on native t-PA has also been found to have an affect on clearance rates of t-PA. WO89/11531 discloses several t-PA variants having additional glycosylation sites, which also have decreased clearance rates. In particular, the T103N extra-glycosylation t-PA mutant exhibited a decreased clearance rate which is five fold lower than native t-PA. Other research has described t-PA variants with reduced glycosylation, which also exhibit decreased clearance rates. (Martin et al., *Fibrinolysis* 4 (3), 9 (1990). Other references describing t-PA glycosylation variants having reduced clearance rates include Ahern et al., Supra, and Collen et al., 1988, Supra. Each of the above references is hereby incorporated by reference.

The methods of the invention require the administration of the thienopyridine derivatives and the thrombolytic agents in effective amounts. An effective amount is one sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone. Effective amounts will depend, of course, on the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment, particularly if acute thromboembolic stroke is the dominant clinical manifestation.

Both the dosage and time of administration of the thienopyridine derivative and the thrombolytic agent vary depending on a number of conditions. The dosage and time of administration can be based on the target blood plasma level of each drug. In order to achieve the target blood plasma level of each drug, the dosing schedule can be manipulated according to patient parameters. For example, if a patient has already received a dosing of a thienopyridine derivative and thus has a circulating plasma level of the thienopyridine derivative which is in the range of the target plasma levels, according to the methods of the invention a thrombolytic agent should be administered in order to achieve target plasma levels of both the thienopyridine derivative and the thrombolytic agent.

Target plasma levels for humans of the active thienopyridine derivative and the thrombolytic agent are well known in the art. Studies involving each class of active compounds at various dosages have been described and include Akaski et al, *Areneim-Forsch/Drug Research*, v. 30, p. 409–414 (1980); Besson and Bogousslavsky, *CNS Drugs*, v. 3(5), p. 351–362 (1995); Sherman D. G. et al, *Chest*, v. 102, p. 529S–537S; Albers, G. W., *Amer. J Card.*, v. 75, p.34B–38B; and Saltiel and Ward, *Drugs*, v. 34, p. 222–262 (1987) all of which are hereby incorporated by reference. In one embodiment the target plasma levels of ticlopidine range from 0.6 to 0.9 mg/liter.

It is expected that oral doses of the thienopyridine derivative in the range of 100 to 1000 mg, in one or several administrations per day, will yield the desired results. A preferred daily dosage of ticlopidine is 500 mg. It is expected that intravenous doses of tPA in the range of 0.05 to 1.5 mg/kg, in one or several administrations, will yield the desired results. A preferred dosage of tPA is 1.1 mg/kg. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

The invention is useful in subjects suffering from thromboembolic stroke. This includes therapeutically treating patients with acute thromboembolic stroke by a variety of administration routes. The particular mode of administration selected will depend of course, upon the particular drug selected, the severity of the thromboembolic stroke being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "oral" includes but is not limited to ingestion via the mouth and enteral ingestion, including via nasal-gastric tubes. The term "parenteral" includes subcutaneous, intravenous, intramuscular, or infusion. Intravenous administration of thrombolytic agents is preferred in emergency situations.

In one embodiment of the invention the thienopyridine derivative and the thrombolytic agent are co-administered intravenously. In another embodiment the thienopyridine derivative and the thrombolytic agent are administered separately. The thienopyridine derivative and thrombolytic agent may be administered by the same method, e.g. intravenous, oral, etc. or may be administered separately by different modes, e.g. thienopyridine administered orally, thrombolytic agent administered intravenously, etc. Oral administration is preferred for the prophylactic administration of thienopyridine derivatives.

Compositions suitable for parenteral administration conveniently comprise a sterile aqueous preparation of the active compound, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1, 3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

EXAMPLES

Example 1

Intravenous Administration of Ticlopidine in Combination with tPA is Effective in Clot Lysis in a Rabbit Model of Thromboembolic Stroke.

Methods:

New Zealand rabbits of either sex (3–3.5 kg) were anesthetized and a 20 ga angiocatheter (Travenol, Deerfield, Ill.) was then introduced into the central ear vein and secured and placed with tape. The catheter was gently flushed with 3 cc of sterile normal saline to insure catheter patency. Ticlopidine hydrochloride, prepared in normal saline, pH 5(5 mg/ml) was administered daily to the animals via the angiocatheter at a dose of 10 mg/kg. All animals were also administered 0.25 cc (I.M.) of streptacillin antibiotic (Phoenix Pharmaceutical, St. Joseph, Mo.) on a daily basis.

After 5 days of ticlopidine administration, the animals were fasted overnight with free access to water. On day 6, the animals were anesthetized and femoral venous and arterial catheters (PE50 and 90, respectively; Clay Adams, Parsippany, N.J.) were placed for subsequent blood sampling, including blood gas and arterial pressure, drug infusions, and fluid replacement. All animals were tracheotomized and mechanically ventilated in order to maintain arterial blood gases within a physiologic range. Arterial blood gas measurements (pH, $pCO_2$, $pO_2$) were determined, using a Corning 168 blood gas monitor. Arterial blood gases were maintained within physiologic range throughout the protocol (pH=7.37–7.42, $pO_2$=124–145 torr, $pCO_2$ 32–42 torr) with hematocrit (28–32%) and arterial pressure (50–60 mmHg) maintained near initial base line values. Platelet aggregation to adenosine diphosphate (ADP; 5–50 $\mu$M) also was reduced from a baseline value of 3.17±1.31 ohms to 0.58±0.51 ohms (mean±SEM; $p<0.05$) prior to embolization.

A clot embolus was prepared by mixing 1 cc of donor rabbit blood with 20 $\mu$ tin granules (50 mg tin/ml whole blood) and placed in PE 90 tubing pretreated with thrombin (Park-Davis, Morris Plains, N.J.). At the time of embolization, the common, external, and internal carotid arteries were all transiently excluded from the circulation and the clot embolus injected into the anterior circulation of the brain via the internal carotid artery. Immediately following clot embolization, regional cerebral blood flow was measured by the hydrogen clearance technique (Young W., *Stroke*, 11:552–564, 1980) within the embolized hemisphere in order to insure a reduction in regional cerebral blood flow to ≦15 cc/100 g/min. Additionally, a submental vertex X-ray confirmed intracranial clot placement. All animals met both criteria. Internal carotid artery patency was restored using 10–0 interrupted nylon sutures (Sharpoint, Reading, Pa.).

Three hours following clot embolization, tissue plasminogen activator (tPA) therapy was initiated. The tPA was administered as a square-wave pulse; i.e., 20% was given intravenously as a bolus, with the remainder infused over a 2 hour period. X-rays were obtained at 1, 2 and 4 hours after initiating tPA administration in order to examine the efficacy of clot lysis.

Seven hours following clot embolization, the animals were euthenized and a calvariectomy was performed. The brain removed from the body was X-rayed in order to determine if there was any residual clot. Significant clot lysis was defined as greater than 75% lysis as determined by measurement of clot length on the radiographs.

Throughout the procedures, animals received Ringer's lactate and 4.2% sodium bicarbonate as needed, in order to maintain adequate volume and pH status, respectively. Platelet aggregation was determined by removing 0.5 cc of whole blood and mixing it with an equal volume of normal saline. Platelet aggregation was examined by the impedance technique using adenosine phosphate (5–50 $\mu$M) using a chronolog whole-blood aggregometer (Havertown, Pa.). All laboratory values were statistically examined using ANOVA repeated measures. Clot lysis rates were compared to tPA controls by Chi square analysis.

Results:

Significant (greater than 75%) clot lysis was observed in all seven animals. Submental vertex X-rays were taken prior to tPA therapy and at 1 hr, 2 hrs, and 4 hrs after the initiation of tPA therapy. Clot lysis was found in all animals (data not shown) by 4 hrs after initiation of tPA therapy. Likewise, the brain X-ray following calvariectomy as well as gross inspection of the brain tissue confirmed clot lysis in all seven animals. In four of the animals, minute, clumped tin fragments were visible on final X-ray. However, no gross hemorrhages were noted in any of the animals either on inspection of the brain surface or following coronal sectioning of the brain.

Therefore, the adjunctive addition of ticlopidine therapy to tPA therapy resulted in enhanced clot lysis (7 of 7 animals examined exhibited lysed clots) over the clot lysis rate of 70.8% (17 of 24 animals) observed in a parallel study in which only tPA was administered at similar time points to the present study (Gross et al., Neurosurgery, 36:1172–1177, 1995). The results of ticlopidine in combination with tPA are in marked contrast with those recently demonstrated in a study in which high and low dose aspirin therapy was utilized concomitant with tPA. In that study, aspirin completely antagonized tPA-mediated thrombolysis.

Example 2

The Effect of Oral Ticlopidine on tPA Mediated Thrombolysis in a Rabbit Model of Thromboembolic Stroke.

Methods:

32 New Zealand white rabbits of either sex, weighing 3–4 kilograms were used for the study. Prior to the start of the experiment, the rabbits were divided into four groups. Each of the four groups was fed a different drug for six days. The groups were divided into those that were administered aspirin at 1 mg/kg, aspirin at 20 mg/kg, ticlopidine at 100 mg/kg and vehicle. The solutions were administered via a 5 Fr. feeding tube (Sherwood Medical, St. Louis, Mo.) by an independent investigator so as to maintain the therapeutic strategies in a blinded manner. Aspirin was prepared in sodium carbonate buffer with a final pH of 7.0. Ticlopidine was prepared in distilled water at a concentration of 5 mg/ml. tPA (Genentech, Inc., San Francisco, Calif.) was prepared in distilled water at a concentration of 6.3 mg/kg.

On day five of the treatment the animals were fasted for 12 hours with free access to water were anesthetized with an intramuscular solution of ketamine (50 mg/kg), acepromazine (20 mg) and xylazine (5 mg/kg). This solution was subsequently used to maintain a surgical depth of anesthesia as determined by responses to various physiologic and autonomic stimuli, including mean arterial pressure and response to paw pinch. The animals were prepared for the surgical procedure as described in Example 1.

Briefly, a midline scalp incision was made to expose the calvarium and bilateral craniectomies were performed in which a temperature sensor was placed in order to measure brain temperature and a 30-gauge platinum-iridium electrodes were inserted 2 mm within the cortical mantle to monitor regional cerebral blood flow via the hydrogen clearance technique. All the instrumentation was carefully fixed in place with fast-setting epoxy. Both core and brain temperatures are maintained within 1° C. of base line values through the use of heating blankets and heating lamps.

Once the surgical procedures had been prepared, the instrumentation was allowed to equilibrate for 30 minutes, prior to embolization. The clot embolus was prepared 4 hours prior to the embolization procedure by gently mixing 1 ml arterial blood with 50 mg tin (20 $\mu$M) granules and introduced into PE-90 tubing pretreated with thrombin.

One hour after embolization a 1.3 mg bolus of tPA was administered to the rabbits, followed by a continuous infusion of 2.5 mg/kg/hr for two hours of tPA. Measurements were taken for a total of 4 hours following clot embolization. At the completion of the study the animals were euthenized, a calveroectomy was performed, and the brain was harvested. The brain was carefully inspected and X-rayed for the presence and position of a residual clot. The brain was then subjected to 2-mm coronal sectioning and incubated in isosmolar TTC at 37° C. for 30 minutes to delineate the region of infarct. Infarct size is determined according to the modification described by Lin et al., *Stroke*, 24:117–121, 1993. Each brain section was also examined for gross hemorrhage.

Following determination of all base line values, the right common carotid bifurcation is exposed, the internal carotid artery (ICA) isolated, a micro-arteriotomy performed and the 15-mm clot embolized intracranially via the ICA. ICA flow is then reestablished via a micro-arteriorrhaphy. Post embolization rCBF is then determined and the experiment continued if rCBF is reduced to 15 cc/100 gm/min. in at least one of the PT-IR electrodes within the embolized hemisphere. The value of rCBF reduction is based on historical studies demonstrating the intensity of ischemia necessary to produce irreversible brain injury, if no therapeutic intervention is instituted. A submental vertex X-ray, using a Phillips dental X-ray machine, verified intracranial placement of the tin-tagged clot. Submental vertex X-rays were repeated every 30 minutes until termination of the experiment. Care was taken to maintain the same position of the X-ray tube relative to the skull. Clot lysis was defined as complete dissolution of the embolus.

Statistical analysis of all hematological variables, ex-vivo platelet and neutrophil function, cerebral blood flow, and infarct size was performed using repeated measures analysis of variance (ANOVA) to detect significant differences between groups and among time points. Individual contrasts were then analyzed if significance was suggested by ANOVA. Due to non-normality of the data, comparison of infarct size between groups was assessed by the Kruskal-Wallis test. Clot lysis was examined by Chi square analysis. Data was expressed as the mean±SEM. Significance was accepted at $\alpha=0.05$.

Platelet and neutrophil activity were determined as follows. Briefly, citrated samples for platelet aggregation were diluted 50:50 with 0.9% saline. A volume of 1 ml was then added to a siliconized cuvette, placed in a preheated 37° C. well within the aggregometer, and stirred at 1000 rpm using a siliconized stir bar. After attaining a stable base line, collagen [2 µg/ml; aspirin and control groups] or thrombin [0.2 µ/ml; ticlopidine] was added to the reaction well. Aggregation was assessed over a 6-minute interval, with the change in impedance (ohms) expressed as the percentage of the baseline value. Samples for neutrophil aggregation and oxygen-free radical release were collected in heparin (10 µ/ml) and diluted in Hank's balanced salt solution (Sigma, St. Louis, Mo.), using a 1:9 dilution. 1 ml of diluted blood was then added to a prewarmed (37° C.) siliconized cuvette and stirred at 400 rpm. Luminol (5 mM; 0.8% dimethyl sulfoxide) was added to the cuvette in order to detect the production of oxygen free radicals by the technique of chemiluminescence. After a stable base line was achieved, formyl-methionyl-leucyl-phenylalanine (fMLP) was added at submaximal doses ($5\times10^{-7}$ M) in order to initiate neutrophil aggregation and oxygen free radical chemiluminescence, both of which were measured simultaneously over a 10 minute interval. Aggregation was calculated as the change in impedance per $10^3$ neutrophils, using the peak height of the reaction. Values were expressed as the percentage of the base line.

A hemocytometer was used to perform cell counts following red cell lysis. Leukocyte differential count was performed by counting 200 leukocytes after Wright-Giemsa staining.

Results:

Hematocrit, arterial blood gases, and mean arterial pressure were monitored and controlled prior to and following clot embolization. These parameters, as well as core and brain temperature, were well maintained throughout the experimental protocol and generally showed no statistical significance in experimental vs. control groups. The final hematocrit in the control group was slightly higher than in other groups (P<0.05). The final arterial pH in the ticlopidine group was slightly lower than in the other groups and the $PaCO_2$ in the aspirin group was slightly lower than in the other groups (p<0.05). However, no changes in each of the parameters were observed to be physiologically significant.

Additionally, platelet aggregation was measured in each of the experimental groups. Blood samples were taken and platelet aggregation was measured prior to treatment, on post treatment day 5, a base line time point on day 6, 0.5 hours after embolization on day 6, and 4 hours after embolization on day 6 of treatment. A significant (P<0.05) reduction in platelet aggregation following the 5 day treatment was noted in the ticlopidine (73.9±12.3%) and high dose aspirin (54.4±11.4) groups, whereas both the vehicle control group and the low dose aspirin group platelet aggregation remained similar to base line pretreatment values. Platelet aggregation was significantly reduced (P<0.01) in each group following the initiation of tPA therapy.

Absolute platelet counts were noted to be very similar throughout both the 5 day treatment protocol and following embolization in the ticlopidine and aspirin groups (Table 1). A moderate rise in the platelet count was noted in the control group throughout this interval, when compared to all other groups (P<0.05, ticlopidine and low dose aspirin, P=0.08 high dose aspirin).

TABLE 1

PLATELET COUNTS

| Group | Pre-treatment | Post-treatment (Day 5) | Baseline (Day 6) Prior to Embolization | 0.5 hr After Embolization | 4.0 hr After Embolization |
|---|---|---|---|---|---|
| Control | 177.6 ± 15.3 | 227.3 ± 14.4 | 237.3 ± 27.3 | 252.0 ± 33.0 | 265.0 ± 14.8 |
| Ticlopidine (100 mg/kg) | 182.9 ± 10.0 | 182.0 ± 18.7 | 207.9 ± 16.8 | 208.0 ± 21.8 | 194.7 ± 13.4 |
| Aspirin (1 mg/kg) | 229.3 ± 22.2 | 219.9 ± 15.4 | 204.3 ± 15.2 | 189.7 ± 19.7 | 212.4 ± 16.2 |
| Aspirin (20 mg/kg) | 199.0 ± 12.4 | 204.3 ± 19.0 | 217.1 ± 18.7 | 226.4 ± 12.7 | 216.9 ± 12.0 |

Counts expressed in thousands $mm^3$; All data expressed as mean ± SEM; low-dose aspirin and ticlopidine groups less than control p < 0.05.

All groups noted a marginal increase in the absolute neutrophil count during the 5 day treatment. (Table 2). Examination of neutrophil activity by stimulated impedance aggregation and luminol dependent chemiluminescence noted very similar results in all groups, that is, a small reduction in aggregation and no effect on chemiluminescence.

TABLE 2

PMN COUNTS AND ACTIVITY
Effect of Anti-platelet Therapy

| Group | PMN COUNTS | PMN AGGREGATION | PMN LDCL |
|---|---|---|---|
| Control | 132.6 ± 15.8 | 59.8 ± 20.9 | 115.3 ± 12.5 |
| Ticlopidine (100 mg/kg) | 112.5 ± 16.4 | 74.7 ± 21.4 | 99.1 ± 20.8 |
| Aspirin (1 mg/kg) | 125.0 ± 20.1 | 71.7 ± 19.2 | 95.2 ± 21.0 |
| Aspirin (20 mg/kg) | 127.3 ± 15.2 | 75.5 ± 20.2 | 93.6 ± 14.6 |

LDCL: luminol-dependent chemiluminescence; PMN: polymorphonuclear leukocyte. All values determined on day 5 of treatment and expressed as a percentage of the pretreatment (day 1) value. All data expressed as mean ± SEM.

Over the 5 day dosing period, animal weights (kg; mean±SEM) remained stable in all groups. With the control (3.6±0.0), low dose aspirin, (3.4±0.1) and high dose aspirin (3.6±0.1) groups without change and the ticlopidine group noting a minimal reduction from 3.5±0.1 to 3.4±0.1.

Brain infarct size was measured following completion of the surgical procedure. Although no group was significantly different from the control group (median infarct size= 10.8%) by the Kruskal-Wallis test, infarct size in both the high dose (P=0.05, median infarct=20.7) and low dose (P<0.05, median infarct size=22.4%) aspirin groups was significantly larger than the ticlopidine group (median infarct size=7.1%, P<0.05). (Data not shown.)

Figure 1:
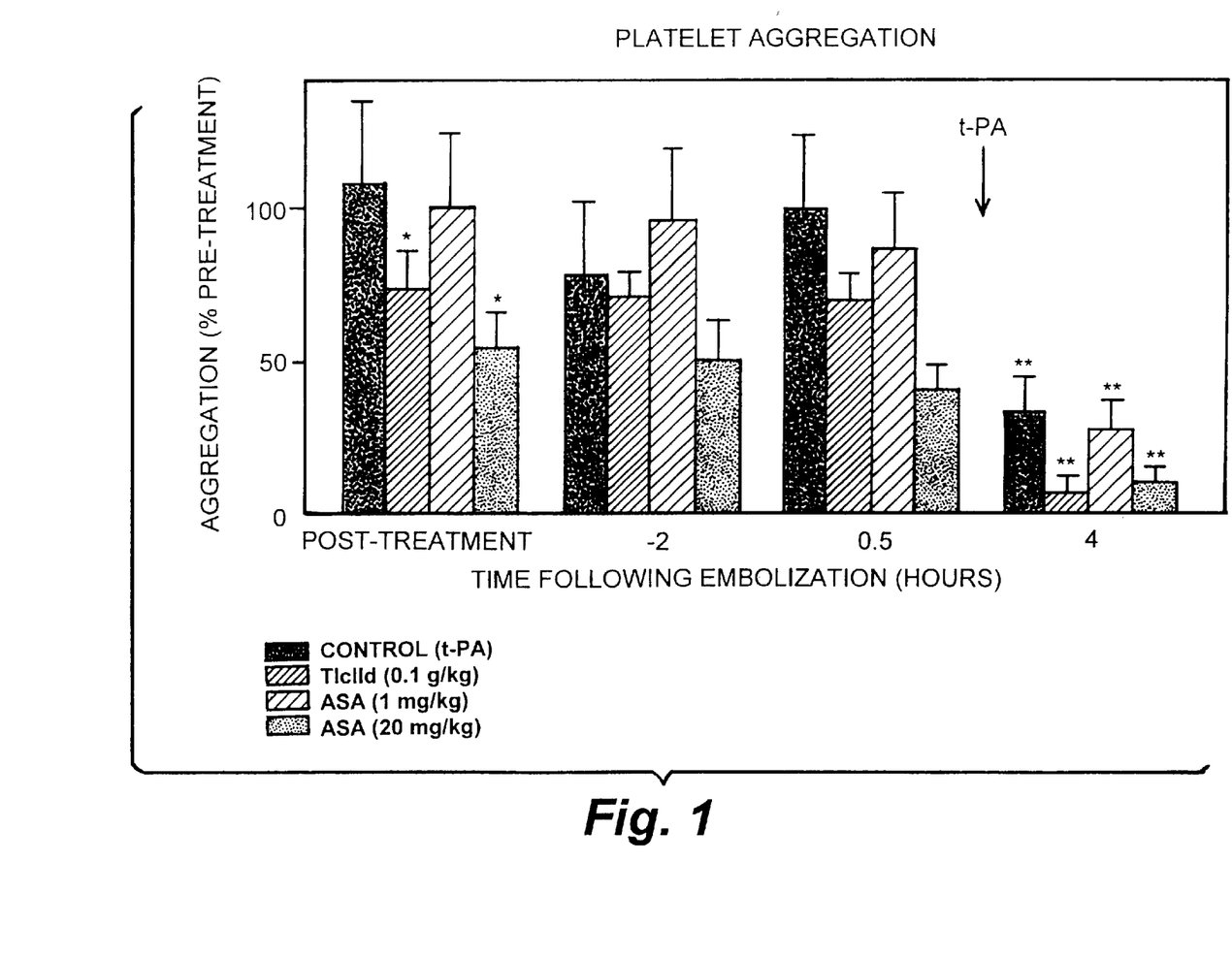
FIG. 1 is a bar graph showing platelet aggregation following a 5-day treatment with aspirin, ticlopidine, or vehicle (post-treatment), and immediately prior to (−0.5 hours) and following (0.5 hours) clot embolization, and following tPA therapy (4 hours), in which ASA is aspirin.
Figure 2:
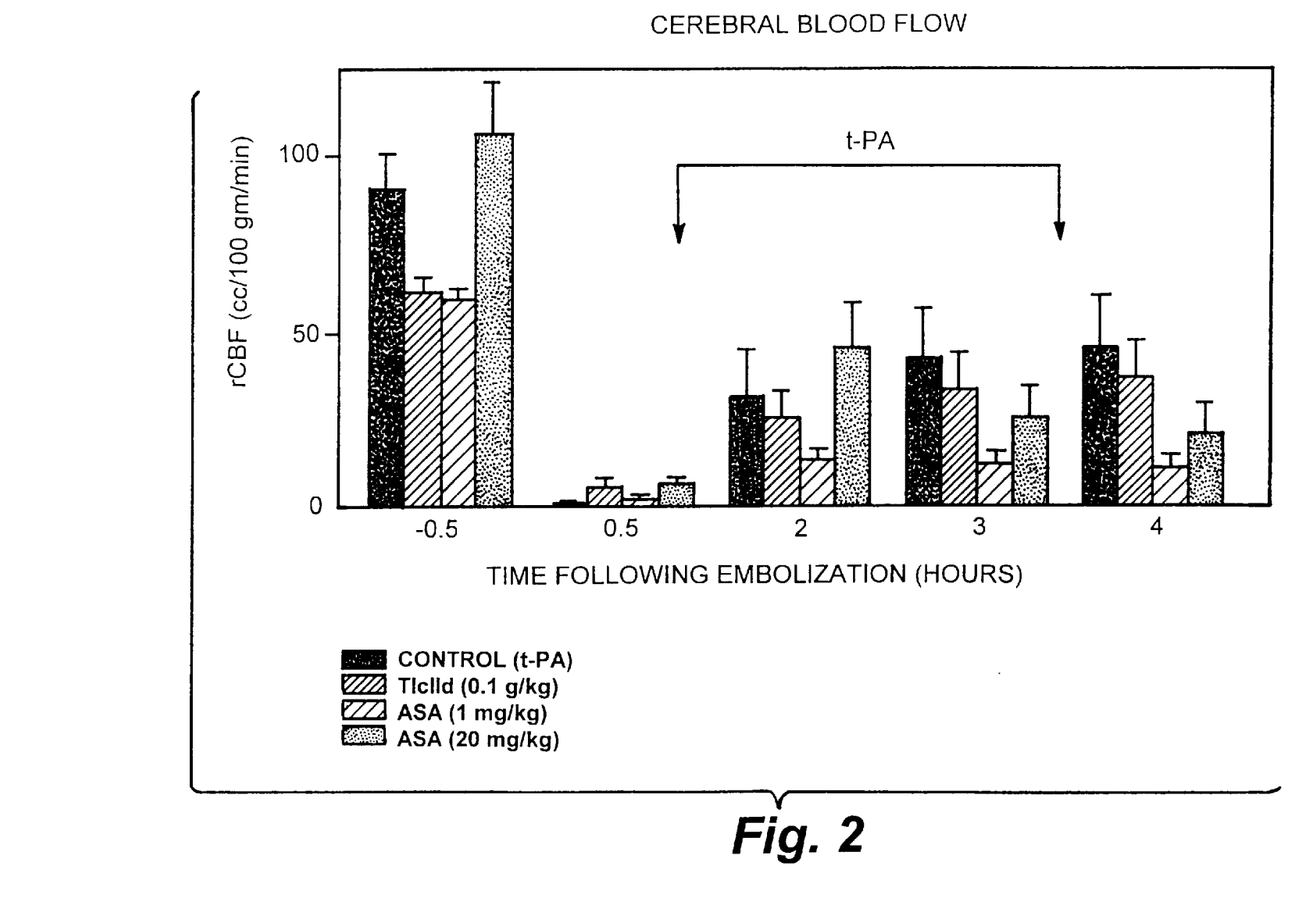
FIG. 2 is a bar graph showing regional cerebral blood flow (rCBF) immediately prior to (−0.5 hours) and at various time points following clot embolization, in which ASA is aspirin, and the crossbar denotes the time of tPA infusion.

Brain infarct size was found to be directly related to the final regional cerebral blood flow (rCBF) value (FIG. 2). Animals in the ticlopidine group exhibited both the smallest infarct size and the greatest improvement in rCBF as a percentage of the base line value. Clot lysis was determined radiographically and confirmed by gross inspection at the conclusion of the experiment. Complete clot lysis was noted in 75% (6 of 8) of control rabbits receiving only tPA. Whereas the ticlopidine group also noted a 75% complete clot lysis rate, aspirin antagonized clot lysis in a dose related manner with 50% (4 of 8) of the low dose and 25% (2 of 8) of the high dose aspirin rabbits demonstrating complete clot lysis.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such equivalents are believed to fall within the scope of the present invention as defined by the appended claims.

We claim:

1. A method for treating thromboembolic stroke, the method comprising the step of:

administering to a subject experiencing a thromboembolic stroke, therapeutically effective amounts of a thienopyridine derivative, wherein the thienopyridine derivative is ticlopidine, and a thrombolytic agent and wherein the thrombolytic agent is tPA, in an amount effective to reduce brain injury which would otherwise occur as a result of the stroke.

2. The method for treating thromboembolic stroke as in claim 1, wherein the ticlopidine is administered in an amount of 250 mg every 12 hours.

3. The method for treating thromboembolic stroke as in claim 1, wherein the thienopyridine derivative is administered orally.

4. The method for treating thromboembolic stroke as in claim 1, wherein the thrombolytic agent is administered intravenously.

5. The method for treating thromboembolic stroke as in claim 1, wherein the tPA is administered in an amount of about 1.1 mg/kg.

6. The method for treating thromboembolic stroke as in claim 1, wherein the tPA is recombinant tPA.

7. The method for treating thromboembolic stroke as in claim 1, wherein the tPA is a modified tPA.

8. The method for treating thromboembolic stroke as in claim 7, wherein the modified tPA is T103N, N117Q, KHRR (296–299) AAAA t-PA.

9. The method for treating thromboembolic stroke as in claim 7, wherein the modified tPA is a vampire bat t-PA selected from the group consisting of Bat-Pa(H), Bat-Pa(I), and Bat-PA(L).

10. The method for treating thromboembolic stroke as in claim 7, wherein the modified tPA is C84S t-PA.

11. The method for treating thromboembolic stroke as in claim 1, wherein the thienopyridine derivative is administered in an amount between 100 and 1000 mg every twelve hours.

12. The method for treating thromboembolic stroke as in claim 1, wherein the thrombolytic agent is administered in an amount between 0.05 and 1.5 mg/kg.

13. The method for treating thromboembolic stroke as in claim 1, wherein the thienopyridine derivative and the thrombolytic agent are administered within a first six hours after the subject experienced the thromboembolic stroke.

14. A method for treating thromboembolic stroke, the method comprising the step of:

administering to a subject who has therapeutically effective amounts of a circulating plasma level of a thienopyridine derivative, wherein the thienopyridine derivative is ticlopidine, and is experiencing a thromboembolic stroke, a thrombolytic agent in an amount effective to reduce brain injury which would otherwise occur as a result of the stroke, wherein the thrombolytic agent is tPA.

15. The method for treating thromboembolic stroke as in claim 14, wherein the circulating plasma level of the ticlopidine is between 0.6 and 0.9 mg/liter.

16. The method for treating thromboembolic stroke as in claim 14, wherein the tPA is administered in an amount between 0.05 and 1.5 mg/kg.

17. The method for treating thromboembolic stroke as in claim 14, wherein the tPA is administered in an amount of about 1.1 mg/kg.

18. The method for treating thromboembolic stroke as in claim 14, wherein the tPA is recombinant tPA.

19. The method for treating thromboembolic stroke as in claim 14, wherein the tPA is a modified tPA.

20. The method for treating thromboembolic stroke as in claim 19, wherein the modified tPA is T103N, N117Q, KHRR (296–299) AAAA t-PA.

21. The method for treating thromboembolic stroke as in claim 19, wherein the modified tPA is a vampire bat t-PA selected from the group consisting of Bat-Pa(H), Bat-Pa(I), and Bat-PA(L).

22. A pharmaceutical preparation, comprising therapeutic effective amounts of:

a thienopyridine derivative, wherein the thienopyridine derivative is ticlopidine, a thrombolytic agent, wherein the thrombolytic agent is tPA, and a pharmaceutically acceptable carrier.

23. The pharmaceutical preparation of claim 22, wherein the pharmaceutical preparation is formulated for oral administration.

24. The pharmaceutical preparation of claim 22, wherein the pharmaceutical preparation is formulated for intravenous administration.

25. The pharmaceutical preparation of claim 23, wherein the thienopyridine derivative is ticlopidine and wherein the thrombolytic agent is tPA.

26. The pharmaceutical preparation of claim 24, wherein the thrombolytic agent is tPA.

27. The pharmaceutical preparation of claim 24, wherein the tPA is a recombinant tPA.

28. The pharmaceutical preparation of claim 24, wherein the tPA is a modified tPA.

29. The pharmaceutical preparation of claim 28, wherein the modified tPA is T103N, N117Q, KHRR (296–299) AAAA t-PA.

30. The pharmaceutical preparation of claim 28, wherein the modified tPA is a vampire bat t-PA selected from the group consisting of Bat-Pa(H), Bat-Pa(I), and Bat-PA(L).

* * * * *